US008858467B2

(12) United States Patent
List et al.

(10) Patent No.: US 8,858,467 B2

(45) Date of Patent: Oct. 14, 2014

(54) LANCING AND ANALYSIS DEVICE

(75) Inventors: Hans List, Hesseneck-Kailbach (DE); Hans-Peter Haar, Wiesloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1348 days.

(21) Appl. No.: 12/574,144

(22) Filed: Oct. 6, 2009

(65) Prior Publication Data

US 2010/0256525 A1 Oct. 7, 2010

(30) Foreign Application Priority Data

Apr. 18, 2007 (EP) .................................... 07007891

(51) Int. Cl.

*A61B 5/00* (2006.01)
*B65D 81/00* (2006.01)
*A61B 5/15* (2006.01)

(52) U.S. Cl.

CPC .................................... *A61B 5/1411* (2013.01)
USPC .......................................................... 600/584

(58) Field of Classification Search

CPC ...... A61B 5/14; A61B 5/1405; A61B 5/1411; A61B 5/1422
USPC ........................... 600/583, 584; 606/181-186
See application file for complete search history.

(56) References Cited

U.S. PATENT DOCUMENTS

| | | | |
|---|---|---|---|
| 5,801,057 | A | 9/1998 | Smart et al. |
| 6,055,060 | A | 4/2000 | Bolduan et al. |
| 6,607,658 | B1 | 8/2003 | Heller et al. |
| 7,025,774 | B2 | 4/2006 | Freeman et al. |
| 2002/0168290 | A1 | 11/2002 | Yuzhakov et al. |
| 2003/0018282 | A1 | 1/2003 | Effenhauser et al. |
| 2003/0083685 | A1 | 5/2003 | Freeman et al. |
| 2003/0171699 | A1 | 9/2003 | Brenneman |
| 2003/0208140 | A1 | 11/2003 | Pugh |
| 2004/0162506 | A1 | 8/2004 | Duchon et al. |
| 2006/0178600 | A1 | 8/2006 | Kennedy et al. |

FOREIGN PATENT DOCUMENTS

| | | | |
|---|---|---|---|
| EP | 1402812 | B1 | 3/2006 |
| WO | 03/083469 | A2 | 10/2003 |
| WO | 2005/104949 | A1 | 11/2008 |

OTHER PUBLICATIONS

English translation of International Preliminary Report on Patentability mailed Oct. 22, 2009 from corresponding PCT case.

*Primary Examiner* — Max Hindenburg
*Assistant Examiner* — Jonathan M Foreman
(74) *Attorney, Agent, or Firm* — Roche Diagnostics Operations, Inc.

(57) ABSTRACT

A lancing device for generating a puncture wound in a body part to obtain a body fluid sample for analytical or diagnostic purposes, in particular, by using integrated disposables that comprise a lancing element as well as an associated test element is disclosed. In order to achieve a high success rate in obtaining the body fluid sample, a drive can be designed such that the lancing element or the test element can be moved into a contact position while remaining in a position near the body part contact opening during a deployment period. If the amount of sample obtained in a lancing movement is inadequate to carry out the analysis or diagnosis, the lancing element can be brought into contact with the sample by a user by manual positioning the lancing device to manually take up a sample obtained by manually milking the sampling site in the region of the puncture wound.

14 Claims, 2 Drawing Sheets

Fig. 1
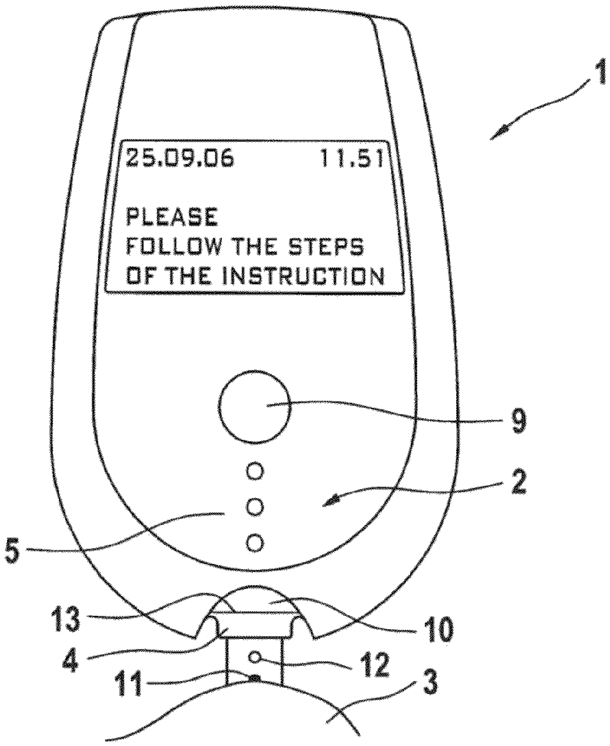
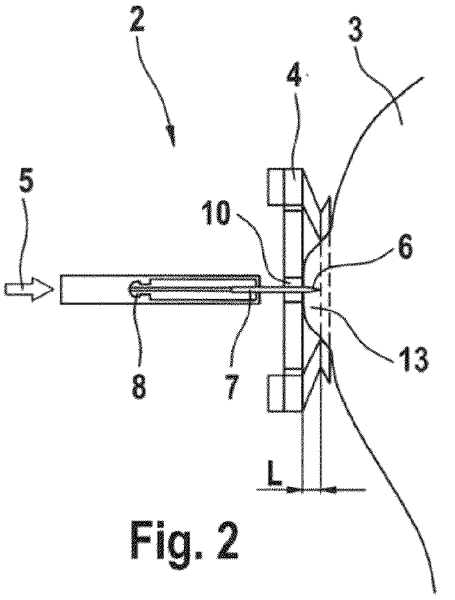
Fig. 2
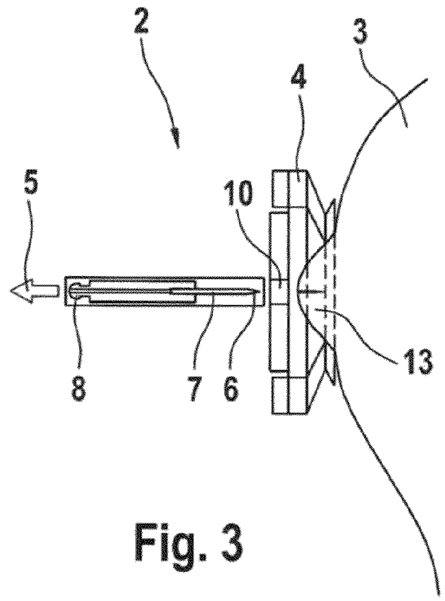
Fig. 3

LANCING AND ANALYSIS DEVICE

CROSS-REFERENCE TO RELATED APPLICATIONS

This application is a continuation of International Application No. PCT/EP08/003,023, filed Apr. 16, 2008, which claims priority to EP 07 007 891.0, filed Apr. 18, 2007.

BACKGROUND

The present disclosure generally relates to a lancing device for generating a puncture wound in a body part of a human or animal to obtain a body fluid sample and, in particular, relates to a lancing device for generating a puncture wound in a body part of a human or animal to obtain a body fluid sample with a first analytical consumable which comprises a lancing element for carrying out an analysis of a medically significant component of the sample with a second analytical consumable which comprises a test element for analytical or diagnostic purposes on the basis of a medically significant component of the sample.

Traditionally, the body fluid sample that is collected, is usually blood. However, in some cases, a interstitial fluid sample may also be obtained. In the following, reference is made to blood as an example of a body fluid without limiting the generality and also as an example for other body fluids that can be obtained from a puncture wound.

Lancing systems usually are comprised of lancing elements, that are typically disposable and intended for single use for piercing into the skin, and a lancing device with a lancing element drive for the lancing movement of the lancing element. The lancing device of such a lancing system has a pressing member for pressing onto the body part in which it is intended to generate a puncture wound and a trigger that enables a user to actuate a puncture movement of a lancing element. Alternatively, the puncture movement can also be triggered automatically by pressing the lancing device onto the skin. The lancing element can be, for example, a lancet, a needle or a needle element. Such lancing elements can, for example, be inserted into a lancing device in a magazine.

Disposable lancing elements have been used for a long time to take a small amount of blood from a body part, usually from a finger or earlobe, for analytical-diagnostic purposes. In one embodiment, the lancing elements are usually referred to as lancets. Lancets, intended for manual puncture, are usually used only by medically trained personnel. Nevertheless, the puncture can be associated with considerable pain.

Lancing devices which contain a lancing element drive have also been used for a long time. It is often necessary to regularly monitor certain analytical values of the blood. Lancing devices can be used in particular by diabetics who have to check their blood sugar level several times daily by means of a blood sugar self-monitoring, in order to maintain their blood sugar Additionally, checking blood coagulation parameters by patient blood coagulation self-monitoring is also widespread. The lancing device can be disposable, i.e. only intended for single, with a permanently integrated lancet. However, as a rule, it can be used many times and has a holder in which one lancet at a time can be coupled interchangeably with the lancing drive. Since the devices and lancets are elements that arc adapted to one another and supplied by the same manufacturer, they are referred to as a "lancing system" or "blood collection system."

A spring, or an electromagnetic drive, is usually used as a drive element for the lancet drive arranged in a housing of the lancing device. A lancet guide ensures that the lancing movement takes place on a predetermined puncture path. In this process, the movement of the lancet towards the skin surface until the reversal point (i.e., propulsion phase of the lancing movement) is driven for example by a spring system, or an electromagnetic drive, and a corresponding drive can be provided for the return movement of the lancet (i.e., return phase of the lancing movement).

Typically, lancing devices have an exit opening from which the tip of the lancet emerges for a short time to generate a wound in a body part against which the lancing device is pressed. The lancing depth is defined by the distance in the puncture direction between the position which the lancet tip reaches at the reversal point of the lancet movement and the plane of a skin contact face which surrounds the exit opening in a ring shape and rests against the skin at the moment of puncture. Hence, the lancing device with the skin contact face forms a lancing depth reference element which ensures that the lancing depth corresponds to a specified value.

In order to control the lancing depth, it is customary to limit the path of travel of the lancet in the puncture direction, for example, by a stop member connected to the lancet which strikes a corresponding stop face in the housing of the lancing device.

Such blood collection systems have to fulfill high demands when it is necessary to regularly monitor certain analytical values of the blood. This applies particularly to diabetics which should frequently check their blood sugar level in order to maintain their blood sugar level within certain target limits by adapting insulin injections to the requirements (which varies greatly depending on the food intake, physical activity etc.). Extensive scientific investigations have proven that an intensive care with at least four blood analyses per day can dramatically cutback severe late sequelae of diabetes mellitus (for example, a retinopathy with resulting blindness of the patient). A prerequisite for this intensive care is that the frequent blood collection is associated with the lowest possible pain.

Consequently, an aim in the development of lancing systems is to generate a puncture wound with as little pain as possible from which a usable sample, i.e. an adequate amount of a body fluid can be collected. The puncture depth is of major importance for the pain sensation as well as for the sample collection. In general, the pain sensation increases with an increasing puncture depth as does the amount of liquid which can be obtained from the puncture wound. Hence, a requirement for lancing devices is only to take a small amount of a blood sample which is sufficient for carrying out the analysis and to arrange for a puncture depth which, on the one hand, is as small as possible and, on the other hand, is as deep as necessary; and there are various developments for making the blood collection as pain-free as possible.

In practice, a blood collection system is, however, not only expected to meet the requirements for a minimal pain sensation but at the same time it should be simple to operate, have a compact slim design and enable a simple, cost-effective construction. On the basis of these practical requirements, blood analysis devices have been and are being developed which satisfy these in some case contrary requirements to as large an extent as possible.

Since the puncture depth should be set to a smallest possible value, it may be the case in practice that no blood sample or an inadequate blood sample is obtained by a puncture. Therefore, endeavors have been made in the prior art to reduce the risk of an unsuccessful puncture. For example, lancing devices with a pressure sensor are known in which a puncture movement is automatically triggered as soon as a pressure presses on the pressing member which exceeds a predetermined minimum pressure.

Whereas in hospitals and doctor's offices several milliliters of blood of a person to be examined are often collected by venepuncture for the analysis in order to thus allow a plurality of laboratory tests to be carried out, nowadays a few μl blood is often sufficient for individual analyses which are directed specifically to one parameter. The collection of small amounts of sample in the range of a few μl or less for determining analytical parameters is especially widespread for the measurement of the blood sugar level but is also for example used for determining coagulation parameters, triglycerides, HBA1c or lactate.

Such small amounts of blood do not require a venepuncture but can be obtained with the aid of a sterile, sharp lancet which is thrust through the skin, e.g. into the finger pad or the earlobe of the person to be examined. This method is especially suitable when the blood sample can be analyzed directly after the blood collection.

The lancets used to obtain body fluid from a body part by generating a small puncture wound usually have a metal lancet needle the tip of which can be sharpened. These lancets must be stored sterilely until use and should be preferably disposed of after use in such a manner that they cannot result in injury. Hence, blood collection systems have been proposed in which the lancets are stored in a lancet storage container in which a plurality of lancets are kept in store for removal from the lancet storage container at a removal position.

A possible embodiment of such a lancet storage container is a drum magazine from which the lancets can be individually removed wherein the lancets are disposed in chambers in the drum magazine which are each individually closed. The used lancets are either disposed of outside the device or outside the analysis device or they can also be returned to the lancet storage container after use for safe disposal.

A blood glucose measuring instrument is a measuring instrument with the aid of which it is possible to qualitatively or quantitatively determine the blood sugar content. Usually for this purpose a puncture wound is generated in a body, a drop of blood is taken, the drop of blood is applied to the test element and the blood glucose content in the drop is determined with the aid of the test element and blood glucose measuring instrument.

Such analysis devices comprise an instrument housing, a measuring device disposed in the instrument housing for carrying out the analysis on a sample obtained with the lancing device and a processor with a software for processing the measured values determined by the measuring device and for processing the analytical measuring data from the measured values which usually takes into account calibration values.

Test procedures which use test elements are widely used for the qualitative and quantitative analysis of components of a liquid sample, in particular, a body fluid of humans or animals. The test elements contain reagents. The test element is brought into contact with the sample for carrying out a reaction. The reaction of sample and reagent leads to a change of the test element which is characteristic for the analysis and is evaluated with the aid of a suitable analysis device. The analysis device is usually suitable for evaluating a very special type of test element of a particular manufacturer. The test elements and the analysis device form mutually matching components and are referred to overall as an analysis system.

Numerous different types of test elements are known which differ in their measuring principle, the reagents used and in their construction. The use of magazines for test elements and/or lancing elements is known in this connection.

With regard to the measuring principle, colorimetric analysis systems are particularly widespread. In these systems, the reaction of the sample with the reagents contained in the test element results in a color change which can be measured visually or by means of a photometric measuring device. In addition, electrochemical analysis systems have become very important where the reaction of the sample with the reagents of the test element results in an electrically measurable change (of an electrical voltage or an electrical current) which can be measured with appropriate measuring electronics. Such analysis systems are also referred to as amperometric systems.

With regard to the configuration of test elements, strip-shaped test elements (so-called test strips) are common and essentially consist of an elongate support layer made of plastic material and test fields mounted thereon. The test fields usually consist of one or more test layers containing reagents. Such test strips are widely used especially for blood and urine analyses.

In a second type of test element, a test field is surrounded by a frame similar to a photographic slide. The test field of this type of test element usually consists of one or more test layers which are held by the frame and contain suitable reagents for colorimetric tests. After applying the sample to the test field and after the test reaction is completed, the color formation can be observed or measured photometrically.

Lancets and suitable devices for them, i.e. so-called "lancing aids," which enable blood to be collected in a manner which is as free of pain and reproducible as possible are available especially in the field of so-called "home-monitoring", i.e. where medical laymen themselves carry out simple analyses of blood and, in this case, especially for the regular blood collection by diabetics that has to be carried out several times daily to check the blood glucose concentration, and, in this case, it is important that it should be possible to simply and reliably operate the blood glucose measuring instrument, and the determination and display of the measurement results should be informative and reliable.

The common analysis devices are so-called stand-alone measuring instruments. These instruments work autonomously, singly and independently. They, therefore, have a display, a measuring device, a power supply and a complete user interface which can for example comprise a keyboard, a display, a signal generator or a user guidance. The intended use and properties of such instruments are defined apart from a few adaptations of the firmware.

A known instrument concept for blood analysis devices is based on the use of "integrated disposables" which are an integrated combination of in each case an analytical consumable (disposable) in the form of a lancing element (needle element for carrying out the puncture) and an analytical consumable (disposable) in the form of a test element (e.g., test chemistry for carrying out the analysis or diagnosis). A lancing element which is integrated into the test element is available or provided for each test element. Thus, in an integrated disposable the first and the second analytical consumable are integrated into an analytical consumable which comprises a lancing element for carrying out the puncture process for collecting the sample of a body fluid as well as a test element for carrying out the analysis of a medically significant component of the sample. Depending on the focus one also refers to a lancing element with an integrated test element or a test element with an integrated lancing element.

The transfer of the blood drop obtained by the lancing element to an analysis sensor or test element is carried out with the aid of a capillary channel which runs in the instrument housing. This is an example of a lancing system whose needle element has a capillary channel through which a body fluid can be transported from the skin into the interior of the lancing unit.

Another example of such a lancing system is described in the U.S. Patent Application US 2003/0018282 A1. Here the lancing unit does not only comprise the needle inserted into the skin with a capillary channel suitable for transporting the sample, but also a detection area containing reagents. Such a lancing unit which simultaneously contains a receiving area for the sample (for example, in the form of a capillary-active suction layer and/or hollow chamber) and preferably also the reagents required for the analysis. These lancing system is also referred to as a "microsampler". With regard to further details on microsamplers reference is made to the above-mentioned U.S. Patent Application and the documents cited therein, in particular the U.S. Pat. No. 5,801,057. Apart from the special features described here, microsamplers of different constructions can be used within the scope of the present disclosure.

Integrated disposables can also be used. Integrated disposables are consumables that comprise a lancing element for carrying out the puncture for obtaining a sample of body fluid, for example, a blood sample, as well as a test element, e.g., a test chemistry for carrying out the analysis of a medically significant component of the sample. Such disposables are often used in suitable magazines which for example are in the form of a strip.

There are a number of integrated tests for blood analysis in the patent literature. However, they tend to only describe the test construction (U.S. Pat. No. 6,607,658 and EP 1402812 A1 as examples of test elements with an integrated lancet or US 2002/0168290 A1 as an example of a sampler with an integrated test chemistry or an integrated sensor). Some publications deal with drives for the lancing element which extend from simple ballistic spring mechanisms (US 2006/0178600 A1) to an electrical direct drive. Furthermore some publications also concern methods which assist the escape of blood by certain movement profiles (e.g. U.S. Pat. No. 7,025,774).

Integrated disposables are for example also described in the documents U.S. Pat. No. 6,607,658 or US 2002/0168290 A1. After a puncture process by a needle element, a sample is subsequently automatically taken up which can take place either directly by the test element, see e.g. U.S. Pat. No. 6,607,658 or by means of a capillary structure of the needle in which case the blood is subsequently guided to the test field. U.S. Pat. No. 7,025,774 for example describes an integrated system with appropriate drive units.

In everyday life, it is not uncommon that after a puncture of the skin, no sample can be obtained, or only an inadequate sample is obtained, be it due to faulty handling or be it due to the fact that the correct depth setting for the puncture had not yet been determined.

However, before the blood can be taken up by the disposable, blood must previously have been automatically expressed which usually takes place by means of a so-called finger cone or ring which exerts the appropriate pressure on the fingertip such that the blood expression step is assisted. Thus, blood can already be collected during the lancing process, e.g., by means of the needle element below the skin or subsequently be collected from the skin surface. In practice, it turns out that the success of the blood expression step and of the blood collection often depends on many other factors (elasticity of the skin, skin temperature etc.) so that the current "success rate" of the expression and blood collection process is not 100%. Since the disposables are usually only intended for single use, the disposable is thus discarded without being used when the collection process is unsuccessful.

Such integrated, or highly integrated, measuring instruments, especially those for mobile use such as home-monitoring, pose various problems: (1) A fresh lancet is used for each blood withdrawal resulting in a lancet magazine that requires more volume in the blood analysis device than the magazine for the test elements. Therefore, in order to reduce the size of the blood analysis device it is desirable to reduce the volume of the lancet storage container, (2) It is assumed that the integrated disposable, i.e. the combined lancing and test element is intended for single use and is discarded after a cycle of use is completed. An unused test is then also discarded when the blood collection did not function. A new disposable has to be used for a new attempt, and (3) For a user of integrated disposables it is very important that the sample analysis is carried out with a very high success rate so that no disposables are wasted due to the costs of these consumables which are higher than those of simple lancing elements or test elements. It is a goal to have a success rate considerably more than 90% and, in practice, almost 100% in order that such a system is accepted by the users. The users to an increasing extent bear the costs for the consumables themselves. According to the prior art, a high degree of technical complexity is necessary to achieve a high success rate.

An analysis device with an integrated lancing device is known from WO 2005/104949 A1 in which a control device checks whether the sample discharged at the puncture site after the puncture with the lancing element is sufficient for carrying out an analysis with a test element. The use of integrated analysis elements comprising a lancing and test element is proposed. If the amount of sample accumulated at the surface of the skin in a puncture process is insufficient to carry out an analysis, this can be reported to the user by means of a signal device. As a result the device is again placed over the puncture wound and a second puncture process is carried out with the same or with another lancing element. An additional quantity of sample can be obtained by an expression device of the instrument which is used to squeeze the puncture site. If the device has been accidently removed from the puncture site after the first puncture process, it is also possible according to this document for the user to manually squeeze the skin in order to obtain fluid and to again place the device over the puncture site in order to thus take up and analyze the sample. The document only describes cases in which an additional puncture takes place automatically if an inadequate amount of sample was obtained. In general once an inadequate amount of sample is detected the procedure is according to the principle: more of the same, i.e. more punctures, greater lancing depth, more milking effort etc., but always while basically retaining the process typical for the device as in the first attempt at sample collection.

A comparable analysis device is proposed in US 2003/0208140 A1. In this case, it is checked whether an adequate amount of sample has been obtained. However, nothing is said on how to proceed when inadequate amount of sample to carry out an analysis is found.

Therefore, there is a need to provide a lancing device or an analysis device with a very high success rate in the collection of a sample of a body fluid which is obtained in a technically uncomplicated manner, especially using integrated disposables.

SUMMARY

According to the present disclosure, a lancing device and a method for preparing a lancing device for generating a puncture wound in a body part of a human or animal to obtain a body fluid sample with a first analytical consumable comprising a lancing element for carrying out an analysis of a medically significant component of the sample with a second analytical consumable comprising a test element for analytical or diagnostic purposes on the basis of a medically significant component of the sample is disclosed. The lancing device can comprise a pressing member for pressing the lancing device against a body part in which it is intended to generate a puncture wound with the lancing element at a sampling site from which a sample is to be taken, a drive for driving a lancing element inserted into the lancing device for a lancing movement of the lancing element along a predetermined lancing path into a lancing position. The lancing movement can comprise a rapid puncture movement which is directly followed by a return movement, a housing with a body part contact opening for the body part. The lancing element can be disposed in the housing in an initial position and at the body part contact opening it can be pierced into the applied body part in the lancing position by means of the drive, and a control device for checking a collected sample with regard to whether the amount of sample obtained is sufficient for carrying out the analysis with a test element.

An analysis device for analyzing a medically significant component of a body fluid, for example blood or interstitial fluid is also disclosed. A qualitative or quantitative analysis can be carried out, i.e. for example, the presence, the absence or the concentration of a certain analyte in a sample can be determined where the sample is obtained using a lancing device as described above which is integrated into the analysis device. Hence, the analysis device can comprises the lancing device such that an analysis apparatus for carrying out an analysis or diagnosis using the sample obtained by the lancing device can be integrated. The portable analysis device can be battery-operated and can be operated by a patient for patient self-monitoring of a medically significant component such as, for example, blood glucose, cholesterol, or blood coagulation.

Thus, the present disclosure not only relates to lancing systems or lancing devices to obtain a drop of blood for a subsequent analysis with another instrument, but also to integrated systems which can be used not only to carry out the blood collection but also the analysis without additional handling steps by the user. This may result, among others things, in limited space for both functions to be accommodated in one instrument housing, which for handling reasons should be as small as possible.

The present disclosure is generally directed towards lancing systems of various types in which the needle element can be inserted into the skin and can be a solid needle, such as the above-mentioned lancets, or a capillary needle, such as, for example, an open capillary or a closed hollow needle. However, any other suitable type of lancets known in the art can be used.

The present disclosure may be particularly suitable for integrated systems in which the functions of blood collection and analysis are combined in one instrument. In the case of microsamplers known in the art, this integration can be achieved by having the reagents and other components required for the analysis present in its sample uptake area. The lancing elements without a capillary channel can also be used in conjunction with the present disclosure in integrated systems whereby the lancing element can be rapidly retracted after the puncture process so that sample liquid discharging from the skin can enter a capillary channel of an analysis element which can be brought into contact with the sample liquid discharging from the skin within the lancing device.

Hence, the analysis devices can generally relates to any combination of analytical consumables in the form of lancing elements, test elements and integrated disposables. The blood transport or the transport of the body fluid can be obtained with the lancing element by means of the puncture from the puncture site to the test element and can take place in any known manner, for example, by an uptake by the lancing element itself with subsequent transport from the lancing element to the test element, e.g. in a capillary, or by an uptake by the test element directly in which case after the lancing by the lancing element the test element can be brought into contact with the puncture site by a suitable drive.

Accordingly, it is a feature of the embodiments of the present disclosure to provide a lancing device or an analysis device with a very high success rate in the collection of a sample of a body fluid which is obtained in a technically uncomplicated manner, especially using integrated disposables. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1 illustrates a view of an analysis device with an integrated lancing device according to an embodiment of the present disclosure.

FIG. 2 illustrates a first puncture process with a lancing device according to an embodiment of the present disclosure.

FIG. 3 illustrates a retraction process of FIG. 2 according to an embodiment of the present disclosure.

DETAILED DESCRIPTION

Figure 4:
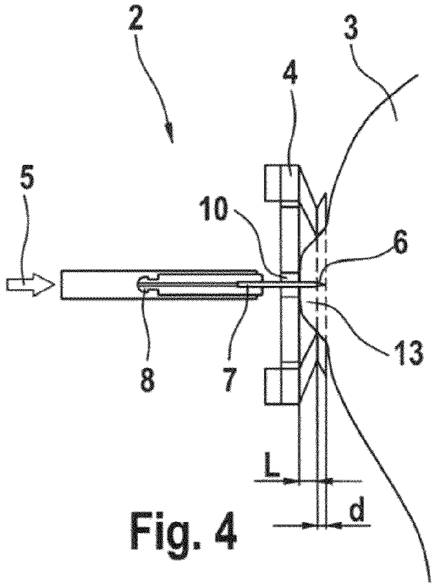
FIG. 4 illustrates a second puncture process with a greater lancing depth according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A lancing device for generating a puncture wound in a body part of a human or animal to obtain a body fluid sample with a first analytical consumable comprising a lancing element for carrying out an analysis of a medically significant component of the body fluid sample with a second analytical consumable that comprises a test element is disclosed. The lancing device can comprise a pressing member for pressing the lancing device against a body part to generate a puncture with the lancing element at a sampling site to obtain a body fluid sample. A drive for driving a lancing element inserted into the lancing device in a lancing movement along a predetermined lancing path into a lancing position. The lancing movement can comprise a rapid puncture movement which is directly followed by a return movement. The lancing device can further comprise a housing with a body part contact opening. The lancing element can be disposed in the housing in an initial position. When in the lancing position and at body part contact opening, the lancing device can pierce the body part by use of the drive.

The drive can be designed such that in a first step of a lancing movement can be carried out with a lancing element to generate a puncture wound at a sampling site for obtaining a body fluid sample. The lancing device can be designed such that, after the lancing movement, a control device can be used to check whether the amount of body fluid sample obtained is sufficient to carry out the analysis with a test element. In a further step, at least one of the analytical consumables can be moved in an extending movement into a contact position in which it can remain in a position near the body part contact opening. During a deployment period, in which at least one of the analytical consumable can be brought into contact with the body fluid sample by a user by manual positioning the lancing device to manually take up a body fluid sample obtained by manually milking the sampling site in the region of the puncture wound. If according to the result of the check carried out by the control device, the amount of body fluid sample obtained is not sufficient to carry out the analysis, the extending movement can remain longer in the contact position than in the lancing position such that in the contact position, at least one of the analytical consumable can be brought into contact with the body fluid sample by the user during the deployment period by a manual positioning of the lancing device to manually take up a body fluid sample which has been obtained by manually milking the sampling site in the region of the puncture wound.

The drive can thus be designed such that at least one of the analytical consumables can be moved into a contact position in which it can remain in a position in the region of the body part contact opening during a deployment period where it can be brought into contact with the body fluid sample by a user by a manual positioning the lancing device to manually take up a body fluid sample obtained from the puncture wound by manually milking the sampling site, if according to the result of a check of the amount of body fluid sample carried out by the control device, the amount of body fluid sample obtained in a previous lancing movement is not sufficient for carrying out the analysis or diagnosis.

Thus, a completely different mode can be adopted in which the device is no longer used as an integrated automatic measuring instrument but rather as a conventional purely manual measuring instrument. The element which should have automatically taken up the body fluid sample in the first attempt can now be offered like a conventional test strip on which the purely manually milked out body fluid sample can be applied in a purely manual manner. If the attempt to automatically obtain body fluid sample from the wound was unsuccessful, the first lancing attempt can generate a puncture wound as if it were a conventional lancing aid.

Only during the manual milking, if it turns out that the puncture was not deep enough to strike blood conveying layers, can it be possible to again automatically use the same test element in the automatic mode as in the first attempt, after increasing the lancing depth. However, this action can be actively invoked by the user.

The disadvantages of the prior art can thus be eliminated by the lancing device according to the present disclosure with a drive unit that can execute the lancing process as well as can carry out a deployment step of the disposable. These functions can also be realized by two separate drives. Manual application of blood can be possible by a new reuse of the lancing element or, in the case of a system for integrated disposables, of the integrated disposable can be made possible so that either the puncture process can be repeated or the disposable can be moved out of the system to enable a manual application of blood by the user after blood has been manually obtained by “milking” of the finger.

The sequence of movements can differ from that of the prior art in that at least one of the analytical consumables (either the lancing element or test element) can be moved by the drive (of the lancing element or of the test element) into a contact position. The analytical consumable can remain in position not only until very shortly before the puncture but can remain in a position near the body part contact opening during a deployment period in which it can be brought into contact with the body fluid sample by a user of the lancing device by manual positioning the lancing device to manually take up a body fluid sample obtained by manually milking the sampling site in the region of the puncture wound, if the result of a check carried out by the control device of the amount of body fluid sample obtained shows that the amount of body fluid sample obtained in a previous lancing movement is not sufficient to carry out the analysis or diagnosis.

The sequence of movements for moving the consumable into the contact position, i.e. the extending movement can be different from the lancing movement for carrying out the puncture in the lancing position because the consumable remains in the contact position for a certain period for the manual application of blood in contrast to the lancing movement which is characterized by a rapid puncture and return movement. The lancing position can be understood as the position of the consumable at the time of the greatest lancing depth into the sampling site. For the sake of simplicity, the lancing position and the contact position can refer to the position of the consumable where it is moved furthest towards the sampling site or extended furthest out of the lancing device, respectively, with respect to its tip. In some embodiments, the selected puncture depth and, thus, the lancing position of the consumable can be adjusted by the user.

The time courses of the lancing and the extending movement can be, however, different because a longer standstill of the Consumable can occur in the contact position, i.e. its movement can be interrupted, whereas in the lancing movement, it can be retracted from the lancing position immediately after the puncture. The duration of the period of standstill of the consumable in the contact position during which the consumable can remain in the contact position for a manual application of blood can be longer than, for example, 0.5 sec, 1.0 sec, 2 sec, 3 sec, 4 sec, 5 sec, 7.5 sec, 10 sec, 12.5 see, 15 sec or 20 sec. This time can be selected to be sufficiently long for the user to carry out the manual application of blood. Therefore, any suitable duration can be used. The consumable can remain in the contact position for a fixed predetermined time period. In other embodiments, the period of stay in the contact position can be ended by a user command when the manual body fluid sample collection has been completed or by a signal of the control device the collection of a sufficient amount of body fluid sample has been detected.

After the first puncture, the lancing device can intentionally be removed from the puncture site and checked to see if the amount of body fluid sample obtained is sufficient to carry out an analysis. If the amount of body fluid sample is insufficient, the puncture site can then milked be and, subsequently, the analysis device can be moved to the collected body fluid sample, or, conversely, the collected body fluid sample on the skin can be moved to the device, such that the body fluid sample liquid can be taken up by the analytical consumable, it can again be applied to the puncture site, the analytical consumable being in the contact position and thus blood can be applied manually as on a conventional test strip. Hence, the lancing device does not automatically proceed with body fluid sample collection, e.g. by again lancing with the same or with another lancing element, but rather the lancing device or analysis device can be removed from the lancing site and can be switched to a manual mode for manually taking up the body fluid sample by the test element.

A switch can be made from a normal operating mode into an alternative sequence in which blood can be taken up manually if underdosing was found. First, a puncture can be made, afterwards it can then be checked whether the amount of body fluid sample obtained is sufficient. If not, the lancing device can change into a manual mode in which additional blood can be obtained by milking the puncture site by hand. Then the blood can be manually applied to the test element that was automatically moved into a suitable position by the lancing device or upon a manual command of the user. Hence, if the examination shows that an inadequate quantity of body fluid sample has been obtained, the measurement may neither be discarded nor does a new puncture take place directly but rather the lancing device can change into the manual mode for the manual application of the blood obtained by milking onto the test element.

In order to simplify the manual blood sampling, the at least one analytical consumable can protrude from an exit opening of the lancing device in the contact position during its deployment period and can protrude to such an extent that the user can easily see the sampling site and can move the lancing device with the protruding analytical consumable to the sampling site. The user can bring the protruding analytical consumable into contact with the sampling site by manually guiding the lancing device towards it.

The analytical consumable, in the further step of the extending movement, can be different from the lancing position which the analytical consumable can be adopted in the first step of the lancing movement. In general, although it can be possible that the contact position and the lancing position be the same, i.e., the analytical consumable moves or is moved exactly to the same extent in the extending movement as in the lancing movement towards the sampling site or out of the lancing device, the analytical consumable can be moved further towards the sampling site or out of the lancing device in the extending movement than in the lancing movement, i.e., the contact position can lie further in the outwards direction of the lancing device than the lancing position so that the user can have a good view of the sampling site and can move the lancing device with the analytical consumable to the sampling site and can contact the analytical consumable with the sampling site by manually guiding the lancing device towards it.

In one exemplary embodiment, the at least one analytical consumable, which can move in into the contact position, can be an analytical consumable comprising a lancing element or a test element or an integrated disposable comprising a lancing element for carrying out the puncture process for obtaining the body fluid sample of a body fluid as well as a test element for carrying out the analysis of a medically significant component of the body fluid sample.

Figure 5:
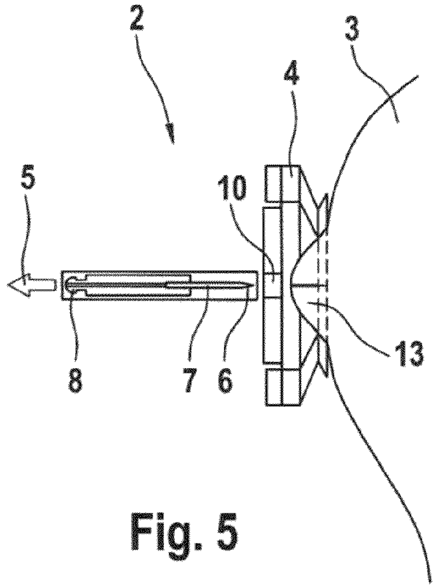
FIG. 5 illustrates a retraction process of FIG. 4 according to an embodiment of the present disclosure.
Figure 6:
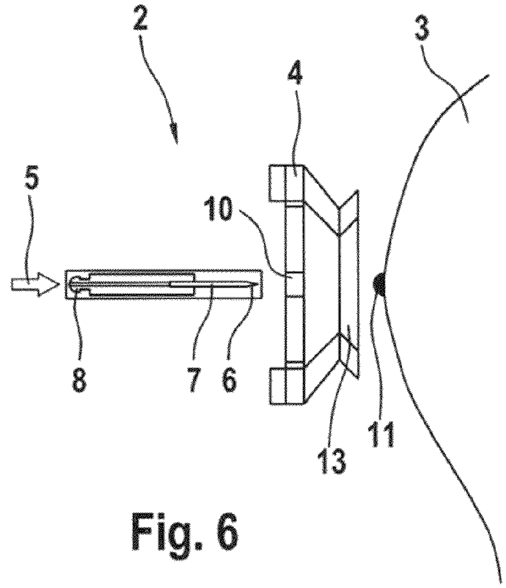
FIG. 6 illustrates a first partial step of a manual blood application on a lancing element according to an embodiment of the present disclosure.
Figure 7:
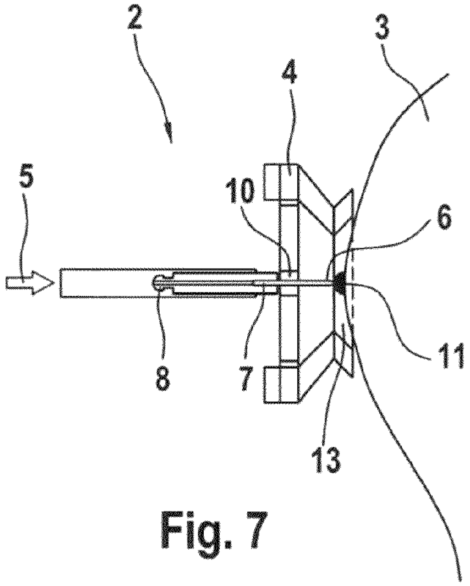
FIG. 7 illustrates a second partial step of FIG. 6 according to an embodiment of the present disclosure.

An exemplary embodiments are shown in FIGS. 2 to 5 and the another exemplary embodiment representing an underdosing case is shown in FIGS. 6 and 7 which will be further discussed below. A lancing device or analysis device can have a standard operating mode (normal operating mode) as well as an additional special state (manual mode) in which the test element can be extended, far out of the analysis device in order that after it has been found that the obtained body fluid sample from a previous puncture process is too small, an attempt can be made to obtain an additional amount of body fluid sample by kneading the puncture site and to bring this additional quantity of body fluid sample into contact with the test element by a manual movement of the lancing device. Hence, the lancing device can comprise an automatic operating mode in which the first step can be a lancing movement with a lancing element to generate a puncture wound at a sampling site for obtaining a body fluid sample. After the lancing movement, the control device can check whether the amount of body fluid sample obtained is sufficient to carry out the analysis with a test element. If according to the result of the check carried out by the control device the amount of body fluid sample obtained in the previous lancing movement is not sufficient to carry out the analysis, the lancing device can have a manual operating mode in which at least one of the analytical consumables can be moved by the drive into the contact position either automatically or by a trigger command of the user. Once in the contact position, the analytical consumable can remain in a position near the body part contact opening during a deployment period in which the analytical consumable can be brought into contact with the body fluid sample by a user by manual positioning the lancing device to manually take up a body fluid sample obtained by manually milking the sampling site in the region of the puncture wound.

In the prior art, the test element is typically used directly to take up blood after an unsuccessful blood collection process and the test element is in the same sampling position that it also adopts for the automatic blood collection process. In contrast, the lancing device according to the present disclosure can enable a body fluid process to take place by a lancing element that firstly carries out a lancing operation. If the body fluid sample is taken up by the lancing element itself, this may require a drive to move the lancing element into a position which may be different from the sequence of movements for the lancing process. In the case of a manual body fluid sample uptake, the lancing element may remain for a longer period in its position for body fluid sample uptake, i.e., in the contact position, the lancing element can be brought into contact with the body fluid sample by manual positioning the lancing device to manually take up a body fluid sample obtained by manually milking the sampling site in the region of the puncture wound. The prior art lancing device, in contrast, has no drive to move the analytical consumable comprising a test element into a sampling position different from the positions of the consumable during the automatic analysis process that can be carried out by the system.

The period during which the analytical consumable can be extended from the device into the contact position near the body part contact opening can be predefined such as, for example, from several seconds to several minutes. After which the drive can automatically retract the analytical consumable into the device or ejects it. The end of the deployment period can be announced to the user by prior signals. In other embodiments, the deployment period can, however, also only be ended by actuation of an operating element by the user.

In one embodiment, the contact made by the user between the body part or body fluid sample liquid and the analytical consumable that takes up the body fluid in the contact position of the analytical consumable, the body part can rest against the body part contact opening in the same position as for lancing. In another embodiment, the body part can also be at a distance thereto so that the user can have a better view of the sampling site and can make the contact.

If the first lancing did not resulted in a successful body fluid withdrawal, the control of success can thus enable the unsuccessful withdrawal to be detected and can allow the previously pricked finger pad with the puncture wound to be kneaded and massaged (i.e., "milked") in order to assist the body fluid circulation and to achieve a discharge of body fluid. The body fluid obtained can then be applied manually to the application site of the analytical consumable for analysis.

This procedure can be more advantageous than a second lancing because a second lancing may not necessarily increase the success rate for obtaining an adequate quantity of body fluid sample, for example, because little body fluid may be present at the previously pricked site due to a poor body fluid flow. The detection of an error occurring in the first lancing and the subsequent manual application of the body fluid sample with prior kneading of the puncture site can have the advantage in practice that even under unfavorable conditions of the sampling site a very high success rate of more than 95% can be achieved when using a lancing element or an integrated disposable, resulting in a greater acceptability for the user.

According to another embodiment, after the first prick with a lancing element, a check of the success of body fluid collection can be interposed. After which the lancing device can be optionally again switched to standby, so that the user can, where appropriate after correcting the lancing depth setting, can again execute a puncture without having to previously replace the lancing element or disposable.

In one exemplary embodiment, the control device can be designed such that the can visually check the amount of body fluid sample. In the case of systems with test elements with an integrated lancet, the user can, for example, visually check that sufficient body fluid sample has been collected. Since the body fluid is not collected automatically but rather has to be milked by hand, this may be particularly easy. Depending on the embodiment, the lancing apparatus can simply be tensioned again or a menu item for repeating the lancing may be selected, after which the lancing drive again goes into standby. This function can be provided in the utilized device (i.e., a lancing device or an analysis device) and can be readily achieved depending on the operating mode.

In another embodiment, the control device can comprise an automatic body fluid sample quantity detection device or underdosing detection device. Once the automatic body fluid detection has ascertained that an inadequate amount of body fluid has reached the test field, the disposable can be automatically deployed for manual body fluid application. An automatic body fluid detection or underdosing detection is sufficiently well-known in the prior art for test strips. Additionally, the system can be additionally able to firstly execute a repeat lancing process before the user can manually apply body fluid.

In systems which automatically obtain body fluid and also automatically transfer the body fluid sample obtained onto the test chemistry, the wetting control of the test chemistry or the test evaluation can, for example, be used to ascertain whether the collection has been successful and where appropriate the same lancing element or disposable can automatically be put into the lancing standby again. Curve-controlled systems according to the One Way Alternating Drive And Cocking (OWADAC) principle can be particularly suitable for this and even ballistic systems can be designed without a major effort such that they can return to the start state without replacing the lancing element or disposable.

In the case of body fluid samplers where the success of body fluid collection can only be ascertained when the body fluid is transferred to the test chemistry, in most embodiments of disposables (lancing elements or integrated disposables) and analysis devices, it may be possible to move the test sequence back by a few steps so that a new attempt can be started with the same disposable. Even in systems where the test elements are stored in magazines, there may be nothing that interferes with a second attempt of body fluid collection using the same disposable. Care may only be taken that no irreversible processes can be used for the various steps in the sequence such as, for example, the winding on of tapes when for space or cost reasons, no rewind function may be provided, or the bending of sheet metal parts for body fluid transfer as in some variants of body fluid samplers.

In conjunction with the Get And Measure (GAM) systems using the disposables, wherein lancing and measuring can be completely integrated in one instrument, an additional optimization can arise which may further increases the user's chances of obtaining an analytical value such as, for example, a blood glucose value.

The control device can comprise a signal unit to signal to the user that the amount of body fluid sample is too small to carry out the analysis or diagnosis. The signal device can emit an optical, acoustic, haptic or any other suitable signal. This signal device can signal the user that, for example, he may have to decide whether he wishes to use the lancing element or the integrated disposable to make a further lancing attempt at the same sampling position or at a different sampling position or would rather carry out a manual sampling application step where the user can enter his decision by actuating an operating element. Accordingly, the lancing element can be moved into the initial or standby position to carry out a further puncture operation with the lancing element. If it is the first use of the lancing element to remove a body fluid sample, i.e. after the first step of a lancing movement with a lancing element and the check whether the amount of body fluid sample obtained thereby is sufficient, an amount of body fluid sample that is too small to carry out the analysis or diagnosis is detected, the drive can be designed such that after carrying out the additional puncture process the at least one of the analytical consumables can be moved into a contact position where it remains in position near the body part contact opening during a deployment period. The consumable can be brought into contact with the body fluid sample by a user by manual positioning the lancing device in order to manually take up a body fluid sample obtained by manually milking the sampling site of the puncture wound. When according to the result of the control device check the amount of body fluid sample obtained in the previous further lancing process is not sufficient to carry out the analysis, a further puncture process can be carried out using a greater lancing depth. In other embodiments, the signal device can also directly signal to the user that a manual body fluid sample application with the lancing element or integrated disposable may have to be carried out next.

In general, the lancing element can be moved into the contact position for the first use of the lancing element to remove a body fluid sample. In one embodiment, an automatic control device can comprise automatically moving the lancing element into the contact position when the control device detects an inadequate quantity of body fluid sample for carrying out the analysis or diagnosis.

Referring initially to FIG. 1, an exemplary embodiment of an analysis device 1 is illustrated. The analysis device 1 can comprise an integrated lancing device 2 for generating a puncture wound in a body part 3, such as, for example, a finger tip, in order to obtain and analyze a body fluid sample from the body part 3 such as, for example, blood, coagulation parameters, triglycerides, HBA1c, lactate or any other suitable analyte component. The analysis device 1 can further comprise a pressing member 4 for pressing onto the finger tip 3 from which the body fluid sample can be taken and a drive 5 for driving a lancing element 6 in a lancing movement. In one exemplary embodiment, the pressing member 4 can be designed as a pressing cone which can generate an increased body fluid pressure in the pressed finger tip 3 and thus can enhance the exit of body fluid from a puncture wound generated by a lancing element 6 inserted into the lancing device 2.

In one exemplary embodiment, the analysis device 1 can be an integrated system for obtaining and analyzing a body fluid sample. The lancing element 6 therefore can contain a capillary channel 7 which ends in an analysis zone 8 treated with test chemicals that can experience a color change dependent on the analyte concentration.

The analysis zone 8 can be irradiated with a light source and reflected radiation can be detected by a detector. The light source can be controlled by a control unit and the signal of the detector can be evaluated by an evaluation unit. The evaluation unit can also control the control unit. The evaluation unit can evaluate the detector signal in order to determine the concentration of the analyte contained in the body fluid sample. In one embodiment, the result of the analysis can be displayed by a display unit, such as, for example, a liquid crystal display.

One particularly high degree of user convenience can thus be offered by lancing devices 2 which not only can generate a puncture wound but can additionally comprise a measuring device for examining a collected body fluid sample. Suitable measuring devices, such as, for example, for photometric or electrochemical analysis, can be contained in commercial handheld analysis devices 1 such as, for example, for determining the blood glucose content. In one exemplary embodiment, a sampling unit and a test field for the electrochemical or photometric determination of an analyte concentration can be integrated into the lancing element 6. Suitable lancing elements can have a capillary channel into which body fluid can enter during a collecting phase and can reach the test field. In such lancing devices, the sampling may not require any additional handling steps by the user which can be an important advantage especially for users whose motory mobility may be restricted by age or disease.

In one exemplary embodiment, the analysis device 1 can have a trigger that can be actuated by a user by pressing the pressing member 4 triggering a lancing movement. In another exemplary embodiment, the trigger can be in the form of a button 9. A safety device can also be provided which can switch the lancing device 2 from a locked state into a triggering state.

In one exemplary embodiment, illustrated in FIG. 2, the first step of the process can comprise a puncture with the lancing device 2 at a puncture depth L of, for example, 1.0 mm. The finger tip 3 can be pressed against the analysis device 1 or the pressing member 4 in the body part contact opening 13 to execute the lancing. FIG. 3 illustrates the position of the lancing element 6 after it has been completely retracted into the lancing device 2. In this position, the lancing element 6 can be visually or automatically checked whether a sufficient amount of body fluid sample has been obtained in the puncture process of FIG. 2.

If there is an insufficient body fluid sample, the second step, illustrated in FIGS. 4 and 5, of a further puncture process can be triggered manually or automatically. In one exemplary embodiment, illustrates in FIG. 4, a puncture process which can be carried out at an increased puncture depth, such as, for example, increased puncture depth increment, d, of 0.5 mm. FIG. 5 illustrates the lancing element 6 in the same position as in FIG. 3 wherein it can again be checked whether a sufficient amount of body fluid sample has been obtained.

If this is not the case, in one exemplary embodiment a third step, illustrated in FIGS. 6 and 7, can be carried out, wherein this step can also be carried out directly after the first step (FIGS. 2 and 3) with omission of the second step (FIGS. 4 and 5). If according to FIG. 3, it is found that an insufficient amount of body fluid sample was obtained, the lancing element 6 still in the initial position (see FIG. 6) can be retracted into the lancing device 2, corresponding to FIGS. 2 and 4, from which according to FIG. 7, it can be moved into a contact position in which it can protrude from the exit opening 10 of the lancing device 2 near the body part contact opening 13 during a certain deployment period in such a manner that it can be brought into contact by a user with the sampling site or with a body fluid sample obtained by manual milking in the region of the puncture site by manual positioning the lancing device 2. The user can previously knead or massage the region around the sampling site to promote the discharge of a blood drop 11 which can then be brought into contact with the tip of the lancing element 6 which can be moved out of the lancing device 2 by the drive whereby a body fluid sample of the blood drop 11 can be taken up by the lancing element 6.

In one exemplary embodiment, the manual uptake of a blood drop 11 with the lancing element 6 can be guided by a stepwise user guidance which can appear on a display of the analysis device 1. In order to simplify the manual collection of the body fluid sample with the lancing device 2, the sampling site can be illuminated by an illumination means integrated into the lancing device 2 or analysis device 1. FIG. 1 shows this illumination 12 in a position of the analysis device according to FIG. 6.

In one exemplary embodiment, the manual sampling, according to the third step, can also take place in that not the lancing element 6 but rather the test element with which the analysis is carried out, which is either a disposable or an integrated disposable, can be manually brought into contact with the body fluid sample to be collected in the region of the body part contact opening 13 by an appropriate manual positioning of the analysis device 1.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A lancing device for generating a puncture wound in the skin of a human or animal to obtain a sample of a body fluid with a first analytical consumable which comprises a lancing element for carrying out an analysis of a medically significant component of the sample with a second analytical consumable which comprises a test element, wherein the lancing device comprises:

a pressing member for pressing the lancing device against a body part in which it is intended to generate a puncture wound with the lancing element at a sampling site from which a sample is to be taken;

a drive for driving a lancing element inserted into the lancing device for a lancing movement of the lancing element along a predetermined lancing path into a lancing position, wherein the lancing movement comprises a rapid puncture movement which is directly followed by a return movement;

a housing with a body part contact opening for the body part, wherein the lancing element is disposed in the housing in an initial position and at the body part contact opening it can be pierced into the applied body part in the lancing position by actuating the drive; and a control device configured for checking a collected sample with regard to whether the amount of sample obtained and taken up by the lancing device is sufficient for carrying out the analysis with a test element, wherein the drive is configured such that in a first step the lancing movement can be carried out with a lancing element to generate a puncture wound at a sampling site for obtaining a sample, and wherein the lancing device is configured such that after the lancing movement the control device can be used to check whether the amount of sample obtained and taken up by the lancing device is sufficient to carry out the analysis with a test element, and wherein the drive is configured such that in a further step at least one of the analytical consumables can be moved in an extending movement into a contact position in which the analytical consumable remains in a position in the region of the body part contact opening during a deployment period, in which the analytical consumable can be brought into contact with the sample by a user of the lancing device by a manual positioning of the lancing device to manually take up a sample which has been expressed by manually milking the sampling site in the region of the puncture wound, if according to the result of the check carried out by the control device, the amount of sample obtained in the lancing movement is not sufficient to carry out the analysis, and wherein the extending movement differs from the puncture movement in that the analytical consumable remains in the contact position for a longer time than in the lancing position such that in the contact position it can be brought into contact with the sample by the user of the lancing device during the deployment period by a manual positioning of the lancing device to manually take up a sample which has been expressed by manually milking the sampling site in the region of the puncture wound.

2. The lancing device according to claim 1, wherein the at least one analytical consumable protrudes from an exit opening of the lancing device during the deployment.

3. The lancing device according to claim 1, wherein the contact position of the analytical consumable in the further step of the extending movement is different from the lancing position of the first step of the lancing movement.

4. The lancing device according to the claim 1, wherein the analytical consumable is moved further towards the sampling site or further out of the lancing device in the extending movement than in the lancing movement.

5. The lancing device according to claim 1, wherein the at least one analytical consumable moved into the contact position in the further step is an analytical consumable comprising a lancing element or a test element or an integrated disposable which comprises a lancing element for carrying out the puncture to obtain the body fluid sample as well as a test element to carry out the analysis of a medically significant component of the body fluid sample.

6. The lancing device according to claim 1, wherein the first analytical consumable and the second analytical consumable are integrated in an integrated disposable comprising a lancing element for carrying out the puncture process to obtain the body fluid sample and a test element for carrying out the analysis of a medically significant component of the body fluid sample.

7. The lancing device according to claim 1, wherein the control device has a visual check of the amount of body fluid sample by the user.

8. The lancing device according to claim 1, wherein the control device comprises an automatic sample quantity detection device or underdosing detection device.

9. The lancing device according to claim 1, further comprising, an automatic operating mode carries out the first step of a lancing movement; and a manual operating mode initiates the further step of a lancing, if the result of the check performed by the control device indicates an insufficient amount of body fluid sample obtained in the previous lancing movement to carry out the analysis.

10. The lancing device according to claim 1, wherein the at least one analytical consumable can be moved into the contact position by the drive if an inadequate amount of body fluid sample is detected by the first step of a lancing movement.

11. The lancing device according to claim 10, wherein the control device further comprises, a signal unit for signaling to the user an inadequate amount of body fluid sample for carrying out the analysis.

12. The lancing device according to claim 10, wherein the control device further comprises, automatically moving the at least one analytical consumable into the contact position when the control device detects an insufficient amount of body fluid sample for carrying out the analysis.

13. The lancing device according to claim 1, wherein the lancing element can be moved into the initial or standby position to carry out a subsequent puncture operation with the lancing element if the check whether the amount of body fluid sample obtained is sufficient indicates that the amount of body fluid sample is not sufficient to carry out the analysis.

14. The lancing device according to claim 1, wherein the subsequent puncture process is carried out with an increased puncture depth.

* * * * *